(12) United States Patent
Ollivier (10) Patent No.: US 11,607,241 B2
(45) Date of Patent: Mar. 21, 2023

(54) EXPLANTATION ASSEMBLY FOR RETRIEVING INTRACORPOREAL AUTONOMOUS CAPSULES

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 539 days.

(21) Appl. No.: 16/129,773

(22) Filed: Sep. 12, 2018

(65) Prior Publication Data

US 2019/0083123 A1     Mar. 21, 2019

(30) Foreign Application Priority Data

Sep. 15, 2017   (EP) ..................................... 17306187

(51) Int. Cl.
| | | |
|---|---|---|
| *A61B 17/3205* | (2006.01) | |
| *A61B 18/24* | (2006.01) | |
| *A61N 1/05* | (2006.01) | |
| *A61B 18/14* | (2006.01) | |
| *A61B 18/00* | (2006.01) | |

(Continued)

(52) U.S. Cl.
CPC .... *A61B 17/32056* (2013.01); *A61B 18/1492* (2013.01); *A61B 18/24* (2013.01); *A61B 90/39* (2016.02); *A61N 1/059* (2013.01); *A61N 1/0573* (2013.01); *A61N 1/375* (2013.01); *A61N 1/3756* (2013.01); *A61N 1/37205* (2013.01); *A61B 2017/00867* (2013.01); *A61B 2018/00357* (2013.01); *A61B 2018/00577* (2013.01); *A61B 2018/00601* (2013.01); *A61B 2090/3966* (2016.02); *A61N 2001/0578* (2013.01)

(58) Field of Classification Search
CPC .......... A61N 2001/0578; A61N 1/0573; A61B 2017/2212; A61B 5/6861; A61B 17/32056; A61B 17/221; A61B 2018/141
See application file for complete search history.

(56) References Cited

U.S. PATENT DOCUMENTS

| | | | |
|---|---|---|---|
| 6,517,551 B1 * | 2/2003 | Driskill ............ | A61B 17/22031 606/113 |
| 2002/0002383 A1 | 1/2002 | Sepetka et al. | |

(Continued)

FOREIGN PATENT DOCUMENTS

| | | |
|---|---|---|
| CN | 103402578 A | 11/2013 |
| CN | 205181870 U | 4/2016 |

(Continued)

OTHER PUBLICATIONS

Partial European search report on European Patent Application No. 17306187, dated Aug. 20, 2018. 6 pages.

(Continued)

*Primary Examiner* — Katherine M Shi
*Assistant Examiner* — Mohammed S Adam
(74) *Attorney, Agent, or Firm* — Foley & Lardner LLP (57) ABSTRACT

The present disclosure relates to an explantation assembly for retrieving an intracorporeal capsule implanted in a tissue of a patient comprising a first tube and a second tube. The first tube comprises a snare and a tissue. The second tube is configured to interact with the snare of the first tube and configured to be attached to the tissue of the patient.

14 Claims, 5 Drawing Sheets

(51) Int. Cl.
*A61B 90/00* (2016.01)
*A61N 1/375* (2006.01)
*A61N 1/372* (2006.01)
*A61B 17/00* (2006.01)

(56) References Cited

U.S. PATENT DOCUMENTS

| | | | |
|---|---|---|---|
| 2007/0079511 A1 | 4/2007 | Osypka | |
| 2012/0109148 A1 | 5/2012 | Bonner et al. | |
| 2012/0259242 A1* | 10/2012 | Vetter | A61B 18/1482 600/567 |
| 2015/0051614 A1 | 2/2015 | Schmidt et al. | |
| 2015/0283376 A1 | 10/2015 | Ollivier et al. | |
| 2015/0335884 A1* | 11/2015 | Khairkhahan | A61B 17/3468 606/129 |
| 2016/0310723 A1* | 10/2016 | Eggen | A61N 1/0573 |
| 2017/0105743 A1 | 4/2017 | Vale et al. | |
| 2017/0281952 A1* | 10/2017 | Shuros | A61B 17/320016 |
| 2018/0318590 A1* | 11/2018 | Kabe | A61N 1/3756 |

FOREIGN PATENT DOCUMENTS

| | | |
|---|---|---|
| CN | 105744987 A | 7/2016 |
| EP | 3 056 157 A2 | 8/2016 |
| WO | WO-2008/042229 A2 | 4/2008 |
| WO | WO-2012/082755 A1 | 6/2012 |
| WO | WO-2016/172106 A1 | 10/2016 |

OTHER PUBLICATIONS

Search Report on European Patent Application No. 17306187 dated Oct. 25, 2018. 1 page.
Chinese Office Action on CN Application No. 201811072362.6 dated Oct. 12, 2020.

* cited by examiner

EXPLANTATION ASSEMBLY FOR RETRIEVING INTRACORPOREAL AUTONOMOUS CAPSULES

CROSS-REFERENCE TO RELATED PATENT APPLICATIONS

This application claims the benefit of and priority to European Application No. 17306187.0, filed Sep. 15, 2017, which is incorporated herein by reference in its entirety.

BACKGROUND

The present disclosure relates to the retrieval of autonomous capsules implanted in the human body, for example, the heart chamber of a patient, and a medical device suitable for such retrieval.

Autonomous capsules intended to be implanted in the human body, particularly, in a heart chamber (atrium or ventricle, right or left) of a patient are more and more commonly used. These capsules are free of any mechanical connection to an implanted technical object (such as the housing of the stimulation pulse generator) or a non-implanted external device such as a programmer or a monitoring device for remote patient monitoring. These "leadless capsules" are to be distinguished from the electrodes or sensors disposed at the distal end of a conventional probe (lead), which is traversed throughout its length by one or more conductors galvanically connecting the electrode or sensor to a generator that in course is connected to an opposite, proximal end of the probe. Autonomous capsules may continuously monitor heart rhythms and deliver, if needed, electrical stimulation, resynchronization and/or defibrillation pulses to the heart in response to detected arrhythmia, for example.

In the case of infected or eroded capsules, or when the lifetime of the capsule (or primary battery installed in the capsule) has expired, retrieval (explantation) of the capsule becomes necessary. The explantation of autonomous capsules is a particularly risky operation because it is necessary, first, to manage the capture of the body and a traction of the capsule using an explantation accessory and, second, to exercise on this body a torque for detaching it from the implantation site (tissue of the heart chamber) wherein it was retained by some anchoring means. This unscrewing torque and the traction force must be large enough to overcome resistance and adhesions resulting from the formation of fibrous tissue at the location of the implantation site.

In the case of endocardial capsules (capsules attached to the inner wall of an atrial or ventricular chamber, as opposed, for example, to the epicardial capsules secured to the outer wall of the heart), the explantation constraints are increased due to, first, the need to go through the peripheral venous system to introduce the explantation accessory and, second, the need to remove the capsule after it is caught and unscrewed/detached while ensuring its withdrawal through the tight curves of the venous system. These maneuvers must be performed both accurately and in a completely secure method.

Explantation accessories, designated as lassos or snares, are commonly used to capture and remove medical equipment such as a lead body, defective catheters, guides, etc., out of the heart chambers and venous system, for example. A snare consists of a flexible wire terminated at its distal end by a deformable loop of shape memory metal, the loop extending in a free state in a plane generally perpendicular to the metal wire that supports it. The metal wire is introduced into the distal orifice of a catheter, crossing therethrough to emerge proximally. The traction of the wire from the proximal end of the catheter has the effect, at the other end, to draw the loop by making it gradually enter the catheter wherein it will be housed.

The surgical operation includes introducing the catheter into the patient's body, with the loop fully folded in the distal end region. The loop is then deployed from the catheter by pushing the wire from the proximal end. Due to the shape memory of the metal, the loop then resumes its snare shape inclined relative to the direction of the wire and of the catheter. The snare can be oriented at will to capture the element to be extracted. Pulling on the wire then makes it possible to partially enter the loop in the catheter, which has the effect of reducing its size and ensuring clamping of the element to be removed.

When handling the snare, it could trap valve tissue or filaments present in the vicinity of the capture, especially when tightening the loop snare. Tissues, and in particular the valve tissues, captured at the same time as the capsule, could be damaged at the time of ex-traction. The risk of tissue capture is increased by the lack of visibility during the operation, which is performed by a practitioner under an image intensifier coupled with X-ray equipment, remote from the explantation site (typically with a femoral access for introduction of the catheter intended to reach the right ventricular cavity). The risk is increased also by the difficulty in controlling the fixation of the snare to the capsule before removing the assembly. Fibrosis and calcification further increase problems in capsule explantation, since they may not allow for the snare approach at all. Such a situation may occur, for example, when the entire capsule or a portion designated for engagement by the snare is covered by fibrosis, in particular, close to a relatively thin wall of (vascular) tissue. Removal of fibrosis tissue poses another risk in form of penetrating the tissue of the wall of a heart chamber (or whatever tissue the capsule is attached to). Moreover, control of a cutting means may be greatly affected, for example, when a relatively thick portion of fibrosis is cut, and empty space behind the cut fibrosis is suddenly encountered by the cutting means. In this situation, there is a high risk of a sudden uncontrolled movement of the cutting means towards the heart wall and puncturing of the same may occur.

SUMMARY

In view of the above, it is an object of the present disclosure to provide an explantation assembly that overcomes the above-mentioned drawbacks of the art.

The above-mentioned problem is addressed by an explantation assembly (explanation accessory) for retrieving an intracorporeal (autonomous, i.e., lead-free) capsule implanted in a tissue of a patient, in particular, attached to a wall of an organ (for example, a wall of a heart chamber) of the patient, according to claim 1. The capsule may be or comprise a cardiac pacemaker. The explantation assembly comprises a first tubular means comprising a snare (lasso) as well as a cutting means and the explantation assembly comprises a second tubular means configured to interact with the snare of the first tubular means and configured to be attached to the tissue of the patient. At least one of the first tubular means and the second tubular means may comprise a catheter. Both the first tubular means and the second tubular means may be configured to be guided to the tissue of the patient transvenously. The second tubular means may be in direct contact with (connected to) the snare of the first tubular means.

Contrary to the art, the explantation assembly comprises both a first tubular means for cutting free the capsule that is to be retrieved and, possibly, for pulling the freed capsule by means of the snare, and a second tubular means that serves for defining a fixed-point in the tissue relative to the first tubular means and allowing control of the operation of the first tubular means by interaction with the snare. The first and second tubular means may be inserted together through the same vein (lower side) or through different veins (first tubular means through lower side and second tubular means through upper side in order to provide accurate and easy placement close to the capsule) of a patient. Connection of the first tubular means to the second tubular means by means of the snare can be achieved in a heart chamber of a patient, for example. In particular, the first tubular means comprises a cutting means for cutting free the capsule in the case that it is covered by some fibrosis. The cutting action is guided at an operation angle that is reliably controlled by the second tubular means attached to the tissue and the interaction of the second tubular means with the snare of the first tubular means.

The cutting means may comprise at least one of a laser means, an electro surgical means including at least one electrode, and a mechanical cutting means including at least one blade. The blade may be retractable or foldable into a body of the first tubular means and/or may comprise at least one electrode for electro ablation. For the same purpose the snare may also comprise at least one electrode.

In particular, the snare may comprise a loop portion (active wire portion) and a linear arm portion (a single branch, for example, a mono-fiber) extending to the loop portion. This allows good control of the movement of the cutting means. When a surgeon pulls the snare the shortening (closing) of the loop portion is symmetric with respect to both sides of the capsule. Thus, movement of the cutting means can substantially be performed along a longitudinal axis of the first tubular means.

According to an embodiment, the second tubular means comprises a (for example, circumferential) groove that is formed in a surface of the second tubular means and configured for receiving the snare of the first tubular means. Such a groove facilitates reliable interaction with the snare of the first tubular means. Moreover, the second tubular means may comprise a helical (screw) member configured to be attached to the tissue of the patient.

According to an embodiment, at least one of the first tubular means and the second tubular means comprises a lumen (channel) configured for administering a contrast medium or for purging the means in order to remove air bubbles prior to introduction into the heart, for example. The lumen may also be used for accommodating a stylet or a guidewire of the first tubular means and the second tubular means during insertion into, and movement in, a vein of a patient. The contrast medium is used in order to allow fluoroscopic determination of the accurate position of the capsule to be retrieved by means of the first and second tubular means. The second tubular means allows for reliably and firmly defining a fixed-point with respect to the operation of the first tubular means. Further, at least one of the first tubular means and the second tubular means comprises a radio-opaque marker facilitating accurate positioning of the first/second tubular means.

According to an embodiment, the first tubular means comprises a tip element comprising at least one guiding groove, preferable two (symmetrically shaped) guiding grooves arranged in parallel to each other, for guiding a portion of the snare offset from a longitudinal axis of the first tubular means thereby defining an operation angle of the snare with respect to the longitudinal axis of the first tubular means.

In addition, the snare employed in the above-described embodiments may be rotatable with respect to an axis (longitudinal and/or latitudinal) of the first tubular means in order to facilitated disengagement from the second tubular means.

Further, an intracorporeal, in particular, intracardiac, capsule assembly is provided comprising an explantation assembly according to one of the above-described examples, an autonomous capsule comprising means for attaching to a tissue of a patient, in particular, to a wall of a heart chamber of a patient, and means for receiving the snare of the first tubular means. The autonomous capsule may be a cardiac pacemaker, for example.

Furthermore, a method is provided of retrieving an intracorporeal, in particular, intracardiac, capsule that is implanted in a tissue of a patient, in particular, a wall of a heart chamber of a patient that is at least partially covered (overgrown) by fibrosis tissue. The method comprises guiding a first tubular means and a second tubular means towards the capsule in the patient's body. The first tubular means and the second tubular means may be together inserted transvenously. The first tubular means comprises a snare and a cutting means and the second tubular means may be connected to the snare. The method comprises positioning the second tubular means close to the capsule and attaching it to the tissue to provide for a fixed-point. Further, the method comprises cutting the fibrosis tissue with the cutting means of the first tubular means under control by the second tubular means via the snare interconnecting the first and second tubular means. In particular, the cutting operation may be performed by tightening the snare. In this case, the cutting operation can be performed from a position relatively close to the tissue (wall of a heart chamber) towards a position relatively far from the tissue (wall of a heart chamber) in order to avoid the risk of perforation of the healthy tissue during the process of removing fibrosis tissue. The snare can be partially guided over the capsule during the cutting process. After the capsule has been sufficiently excavated from the fibrosis tissue it can be retrieved from the body of the patient. The retrieval can be performed by the first tubular means and the snare, or by other suitable means.

During the procedure of cutting the fibrosis tissue (for example, by photo ablation, electro ablation and/or mechanical cutting), the first and second tubular means may be positioned close to the capsule (about 2 times to 0.1 times the diameter of the capsule spaced apart from the capsule, for example) or even on the capsule and may be positioned close to each other (the distance of the longitudinal axis may be in the range of 2 times to 0.1 times the longitudinal extension of the capsule) such that relative movements between the tubular means and the capsule, for example, caused by heart beats, can be kept small. Thereby, high accuracy of the cutting procedure can be guaranteed and fully tested by the physician before activation of the cutting means. Particularly, a physician is enabled to check a trajectory under X-ray observation by pulling the snare. Contrary to the art, the trajectory is easily reproducible.

The above-described method may comprise detaching the snare from the second tubular means after completion of the cutting process, and it may additionally comprise connecting the snare to the capsule and removing the capsule by rotating and pulling the first tubular means. All means described above may be used in the method of retrieving the capsule in any combination that is considered suitable. The capsule to be retrieved by the method can be or comprise a pacemaker.

Furthermore, a medical device is provided herein, comprising a guiding catheter, a snare and means for controlling (transfer of) a torque between the guiding catheter and the snare. The snare may comprise a loop portion and a linear arm portion extending to the loop portion.

The means for controlling the torque is in direct mechanical contact with a portion of the snare. In the art, it is very difficult to accurately operate the snare, particularly, during attachment to an implanted object. When a surgeon, for example, intends a rotational movement of the snare he rotates the body of the snare. However, the snare body is usually made of a highly elastic material and, therefore, any torque applied to the snare body is not directly (and even not linearly) transferred to an end portion of the snare. In order to overcome this problem, a means for controlling the (transfer of) torque is provided. This means can be a mechanical means allowing for any torque applied to the guiding catheter to be transferred directly and linearly to the snare. The means for controlling the torque may permit a high torque transfer along the body thanks to the guiding catheter combined with a tip element attached to, or being made of (for example, drilled of), a part of the guiding catheter, and allow a fixed spatial relationship between the catheter and a portion of the snare that is attached to the catheter by the tip element. The tip element may be distinguished from an end portion of the catheter (body). For example, the tip element is attached to the end portion of the catheter or manufactured from a tubular end portion of the catheter. In particular, the tip element may comprise at least one guiding groove for accommodating a part of the snare.

BRIEF DESCRIPTION OF THE DRAWINGS

Additional features and advantages of the present disclosure will be described with reference to the drawings. In the description, reference is made to the accompanying figures that are meant to illustrate preferred embodiments of the disclosure. It is understood that such embodiments do not represent the full scope of the disclosure.

DETAILED DESCRIPTION

The present disclosure will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein.

The following embodiments are described in sufficient detail to enable those skilled in the art to make use of the disclosure. It is to be understood that other embodiments would be evident, based on the present disclosure, and that system, structure, process or mechanical changes may be made without departing from the scope of the present disclosure. In the following description, numeral specific details are given to provide a thorough understanding of the disclosure. However, it would be apparent that the embodiments of the disclosure may be practiced without the specific details. In order to avoid obscuring the present disclosure, some well-known circuits, system configurations, structure configurations and process steps are not disclosed in detail.

Figure 1A:
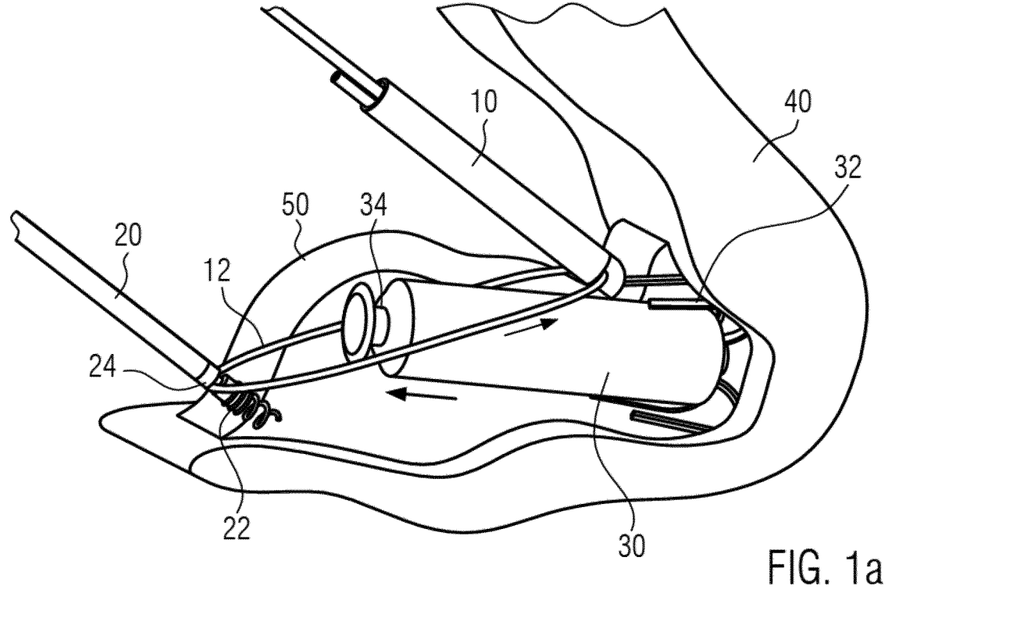
FIGS. 1a and 1b illustrate an explantation assembly according to embodiments of the present disclosure.
Figure 1B:
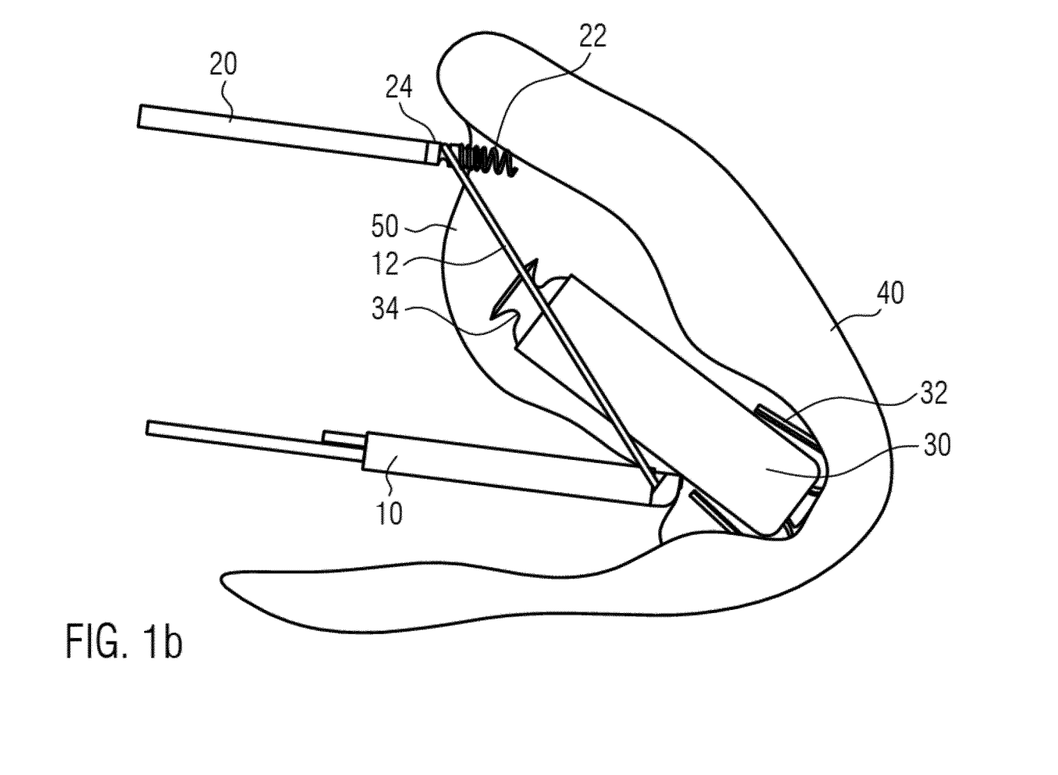

An exemplary explantation assembly (and intracorporeal capsule assembly comprising such an explantation assembly) according to embodiments of the present disclosure is illustrated in FIGS. 1a and 1b. The explantation assembly comprises a first tubular means 10 and a second tubular means 20. Each of the first tubular means 10 and the second tubular means 20 may comprise a (guide) catheter (for example, made of a wire mesh material and having a diameter of 2 to 3 mm) with a lumen through which administration of a contrast medium (fluid) can be provided. A central lumen may be dedicated to the insertion of a stylet or guidewire in order to facilitate accurate placement in the chambers. The stylet is used to increase stiffness of the first and second tubular means 10 and 20. The guidewire may be used for movement of the first and second tubular means 10 and 20 in the vein. Further, the first tubular means 10 and the second tubular means 20 may comprise a radio-opaque marker facilitating accurate positioning of the same. The radio-opaque marker may comprise BaSO4, or TiO2, for example.

An intracorporeal capsule assembly comprises the first tubular means 10 and the second tubular means 20 and an autonomous capsule 30 that may comprise a cardiac pacemaker. The autonomous capsule 30 is free of any mechanical connection to an implantable technical object (such as a housing of the stimulation pulse generator) or non-implantable external device such as programmer or monitoring device for patient remote monitoring. The capsule 30 may comprise a hermetically sealed housing and, located in the interior of the housing, a primary battery for providing power for pacing, sensing and communication and circuits for sensing cardiac activity and generating pacing pulses via electrodes comprised in the capsule 30. Moreover, the capsule 30 may have a diameter of about 4 mm to 8 mm and a length of about 30 mm to about 50 mm.

The first tubular means 10 and the second tubular means 20 are designed for retrieval of the capsule 30 through a patient's blood vessel, for example. For example, the capsule 30 may have to be retrieved due to infection or the end of life of the primary battery. The capsule 30 comprises an anchoring means 32. The capsule 30 is attached to a wall 40 of a heart chamber (inside—atrium or ventricle, right or left—or outside of the heart chamber) by the anchoring means 32. The anchoring means 32 can be or comprise an active, electrically conductive screw for collecting cardiac depolarization potentials and/or for applying of stimulation pulses under the control of a corresponding circuit arranged in the interior of the capsule 30. The description of retrieval of the capsule 30 provided in the disclosure is not limited to the heart, but, may be applied to retrieval of a capsule 30 implanted in some other tissue/organ of a patient.

In the situation depicted in FIGS. 1a and 1b, the capsule 30 is partially covered by fibrosis tissue 50. In particular, the fibrosis tissue 50 covers a circumferential capture groove 34 of the capsule 30. More than one circumferential capture groove 34 may be provided if considered suitable. The circumferential capture groove 34 of the capsule 30 may extend along a curvilinear outline globally oriented in an oblique plane relative to the longitudinal axis of the capsule 30 that may have a generally tubular shape. In particular, the curvilinear outline may be arranged at an angle of between 80° and 100° relative to (measured from) the longitudinal axis of the capsule 30.

The first tubular means 10 comprises a snare 12 by which the capsule 30 can be retrieved using the circumferential capture groove 34. The snare 12 may have a constant diameter of 10 mm to 30 mm. A snare such as the GN2000 Gooseneck of the Covidien company, with a loop diameter of 15 to 20 mm, may be used, for example. The depth and/or width of the circumferential capture groove 34 may be in the range between 1 and 3 times the diameter of the snare 12. The snare 12 may be made of some shape memory metal or metal alloy comprising material, such as nitinol, for example, allowing the snare 12 to re-gain its rounded loop once emerged from the first tubular means 10. A material such as a MP35N alloy or a steel containing a radio-opaque material (for instance, a platinum-iridium alloy), so that the snare loop can be visualized under fluoroscopy coupled to X-ray equipment, may be suitably used for the manufacturing of the snare 12.

It is noted that the first tubular means 10 is not necessarily used for retrieving the capsule 30 by pulling action. Alternatively, the first tubular means 10 may only be used for cutting free the capsule 30 and the thus separated capsule 30 is eventually removed from the patient's body by some other means. In any case, the first tubular means 10 comprises the snare 12 for interaction with the second tubular means 20.

The first tubular means 10, furthermore, comprises a cutting means that will be described in more detail below and is used for cutting the capsule 30 free from the fibrosis tissue 50. The operation of the first tubular means 10 is controlled/guided by means of the snare 12 and the second tubular means 20. The second tubular means 20 comprises a helical member 22 to attach to the cardiac tissue 40. Any other form of the anchoring member may, alternatively, be chosen. Moreover, the second tubular means 20 comprises a circumferential groove 24 for receiving and securing the snare 12. More than one circumferential groove 24 may be provided if considered suitable. The circumferential groove 24 of the second tubular means 20 may extend along a curvilinear outline globally oriented in an oblique plane relative to the longitudinal axis of the second tubular means 20. In particular, the curvilinear outline may be arranged at an angle of between 80° and 100° relative to (measured from) the longitudinal axis of the second tubular means 20. The depth and/or width of the circumferential groove 24 of the second tubular means 20 may be in the range between 1 and 3 times the diameter of the wire of the snare 12.

By attaching the second tubular means 20 to the tissue 40 via the helical member 22 a fixed-point for the operation of the first tubular means 10 is defined. The fixed-point may suitably be defined very close to the capsule and in spatial continuation of the longitudinal axis of the capsule 30. The operation angle of the first tubular means 10 is determined by that fixed-point and the snare 12 of the first tubular means 10 that interacts with the second tubular means 20 via the circumferential groove 24 of the same. Thus, any cutting operation performed by a surgeon by means of the first tubular means 10 can reliably be controlled. In particular, the provided explantation assembly allows for a cutting operation starting close to the tissue to which the capsule 30 is attached, i.e., in the described examples, close to a wall of a heart chamber, and preceding in direction away from this wall. Thereby, any violation of the tissue/wall (e.g., injury, perforation) of the heart chamber during the process of cutting fibrosis tissue can effectively by avoided.

Figure 2A:
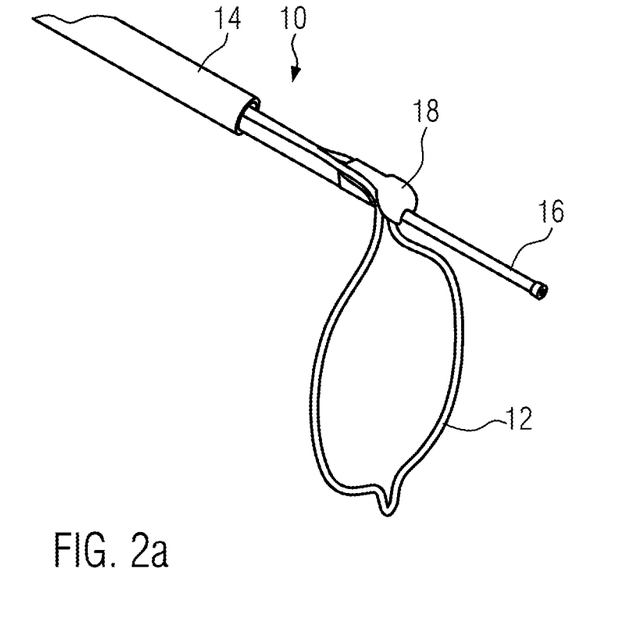
FIGS. 2a to 2c illustrate a tubular means comprising a snare and a laser means being part of an explantation assembly according to embodiments of the present disclosure.

FIGS. 2a to 5 illustrate various examples of the first tubular means 10. As shown in FIG. 2a, the first tubular means 10 comprises a sheath (for example, a catheter shaft that may be covered by a protective liner) 14 that may be made of or comprise a suitable metal material. The snare 12 is guided in the interior of the sheath 14 and may be moved, as known in the art, by a snare slider (not shown in the figures). In particular, the snare 12 comprises a single linear arm guided in the first tubular means 10 and extending to a loop portion used for the connection to the second tubular means 20. Thereby, when a surgeon pulls the snare 12, a shortening (closing) of the loop portion is symmetric with respect to both sides of the capsule 30 is achieved and a laser means 16 can move along a longitudinal axis of the first tubular means 10. Moreover, the laser means 16 may be housed in the sheath 14. The laser means 16 can be connected to a laser source (not shown in the figures), for example, an excimer laser. In addition, the first tubular means 10 comprises a tip element 18 (shown displaced axially from the end of the first tubular means 10 in FIG. 2a for illustration purposes).

Figure 2B:
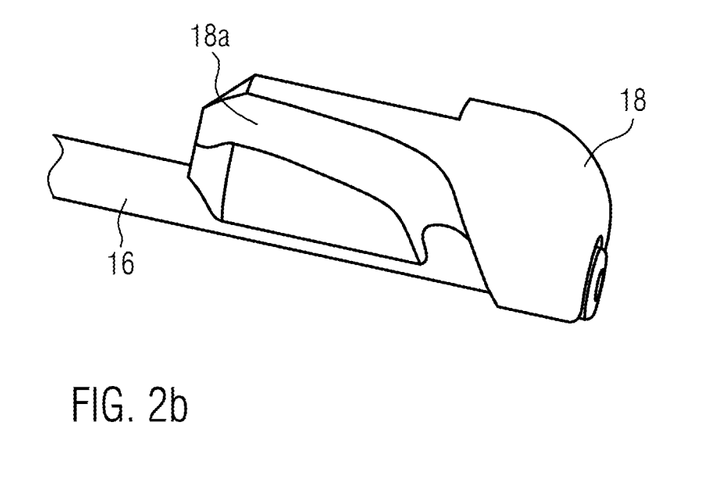
Figure 2C:
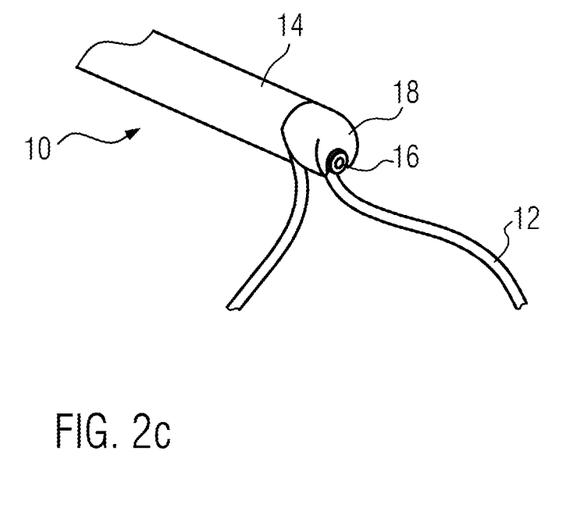

The snare 12 is partially guided in guiding grooves 18a formed in the tip element 18 as illustrated in FIG. 2b. FIG. 2c illustrates the completely assembled first tubular means 10 comprising the snare 12, the laser means 16 and the tip element 18 in its final operating position. The guiding grooves 18a allow for a well-defined spatial relation (angle) between the longitudinal axis of the first tubular means 10 and the snare 12 thereby facilitating operation of the first tubular means 10 by a surgeon. In particular, due to the provision of the guiding grooves 18a, the guidance of the snare 12 will be insensitive to residual torques present in the first tubular means 10. Any torque applied by the surgeon to the first tubular means 10 can be readily transferred to the snare 12 by means of the tip element 18. The portions of the snare 12 received in the guiding grooves 18a may comprise a radio-opaque material. The tip element 18 may be formed of a suitable plastic material (for example, a thermoplastic polymer).

Figure 3:
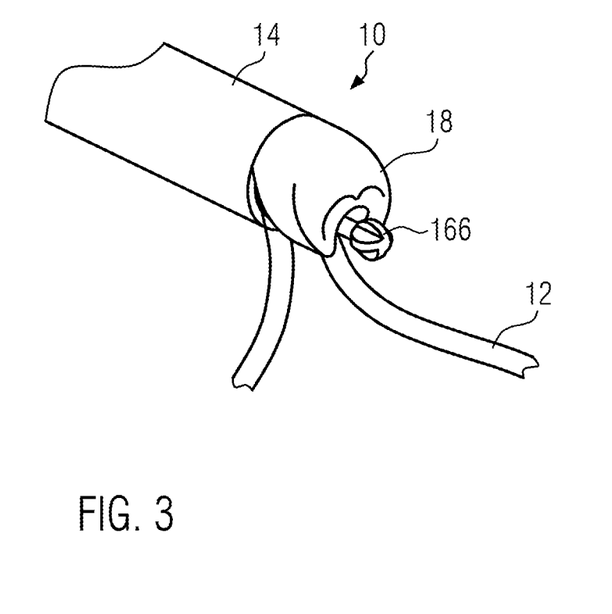
FIG. 3 illustrates a tubular means comprising a snare and a mechanical cutting means in form of a rotatable blade being part of an explantation assembly according to embodiments of the present disclosure.

FIG. 3 shows another embodiment of the first tubular means 10. Instead of a laser means 16, the first tubular means 10 shown in FIG. 3 comprises a rotatable blade (milling cutter) 166 for cutting tissue, in particular, the fibrosis tissue 50 shown in FIGS. 1a and 1b. The other components (snare 12, sheath 14 and tip element 18) may be similar to or the same as described above with reference to FIGS. 2a to 2c.

Figure 4:
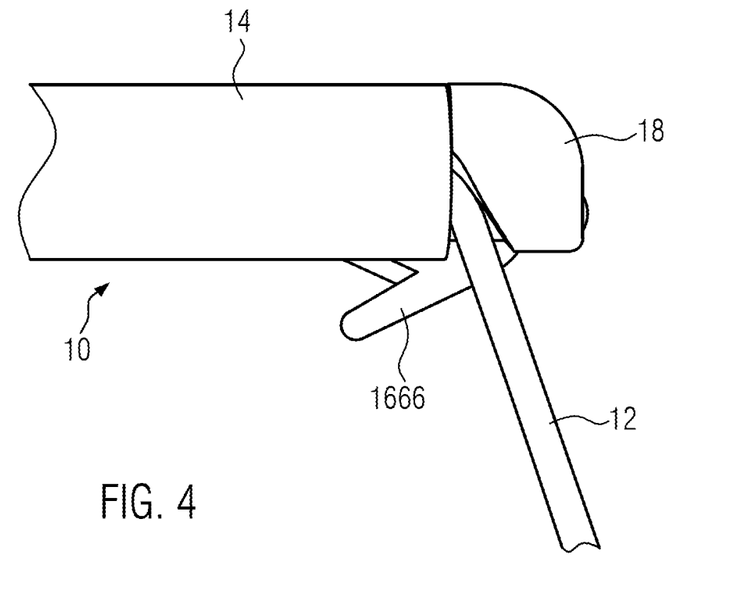
FIG. 4 illustrates a tubular means comprising a snare and a mechanical cutting means in form of a retractable blade being part of an explantation assembly according to embodiments of the present disclosure.

FIG. 4 shows another embodiment of the first tubular means 10. Similar to the embodiment shown in FIG. 3, a mechanical cutting means is provided. In this embodiment, however, the mechanical cutting means is provided in form of a retractable blade 1666. The blade 1666 may also comprise electrodes for electro ablation of tissue. The other components (snare 12, sheath 14 and tip element 18) may be similar to or the same as described above with reference to FIGS. 2a to 2c.

Figure 5:
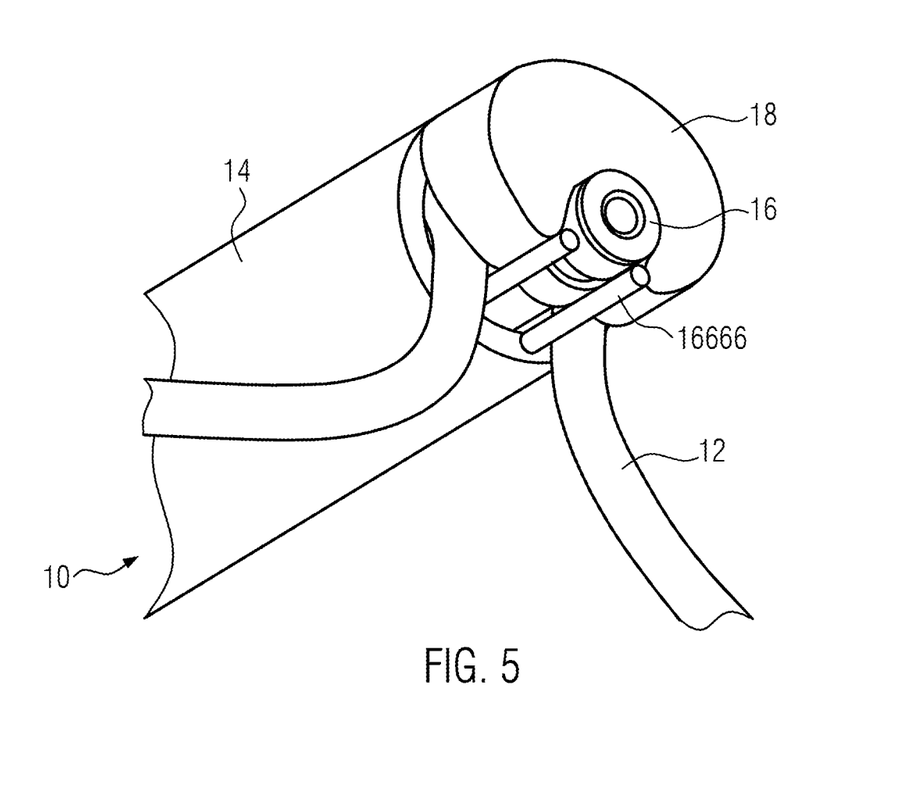
FIG. 5 illustrates a tubular means comprising a snare and a laser means as well as heating electrodes for electro ablation being part of an explantation assembly according to embodiments of the present disclosure.

FIG. 5 shows another embodiment of the first tubular means 10. The first tubular means 10 of this embodiment comprises a laser means 16 and, additionally, a pair of electrodes 16666 provided for elector ablation of tissue. An RF current may be applied to the electrodes 16666 via a wire housed in the sheath 14. The electrodes 16666 may have diameters in the range of 0.2 mm to 0.4 mm and they may be operated to provide a bipolar or monopolar cut mode. The other components (snare 12, sheath 14 and tip element 18) may be similar to or the same as described above with reference to FIGS. 2a to 2c.

It is noted that two or more of the different cutting means 16, 166, 1666 and 16666 may be combined in the first tubular means 10 as desired. Furthermore, the snare 12 may also be configured for electro-surgery, for example, by providing electrodes on the snare 12.

A capsule retrieval operation by means of the above-described embodiments of the present disclosure may be performed (preferably, during continuous radiological monitoring) as follows (reference is made to the above-described figures). Both the first tubular means 10 and the second tubular means 20 are inserted into the patient's body and guided to the field of operation. The first tubular means 10 may be guided from a hip vein to the heart chamber and the second tubular means 20 may be guided from a vein above the heart to the heart chamber. The second tubular means 20 may already be connected to the first tubular means 10 via the snare 12 of the first tubular means 10. The accurate location of the capsule 30 has to be determined. This step can be performed by standard fluoroscopy using some contrast medium that can be injected using the first tubular means 10 and/or the second tubular means 20. Positioning of the second tubular means 20 in the vicinity of the accurately localized capsule 30 is performed in a following process step. The second tubular means 20 is attached to cardiac tissue 40 by means of the helical member 22. Thereby, a fixed-point is defined that can be used in operation of the first tubular means 10. Suitably, this fixed-point has no or almost no off-set to the longitudinal axis of the second tubular means 20.

Then, the first tubular means 10 is advanced to the vicinity of the capsule 30. During the advancement of the first tubular means 10 the snare 12 remains connected to the second tubular means 20 via the circumferential groove 24 of the latter. In particular, in operation, the first tubular means 10 can be kept in immediate proximity to the capsule 30 by means of the snare 12. The fixed-point defined by the second tubular means 20 by attachment to the cardiac tissue 40 can be employed during operation of the first tubular means 10 due to the interaction of the first tubular means 10 and the second tubular means 20 via the snare 12. A portion of the snare 12 may be supported (directly or with intermediate fibrosis tissue being present) by a portion of the body of the capsule 30. In particular, this interaction provides for a well-defined operation angle of attack of the fibrosis tissue 50 (see, particularly, FIGS. 1a and 1b). Femoral access of the first tubular means 10 is preferred, since this allows retrieval of the capsule 30 through the same path used for insertion of the first tubular means 10.

Guided by the snare 12, a cutting operation (electro ablation, laser ablation or mechanical ablation) of fibrosis tissue 50 is performed in order to expose, at least partially, the capsule 30, particularly, the circumferential capture groove 34 of the capsule 30. The cutting operation is performed by means of a cutting means comprised in the first tubular means 10. During the cutting operation (electro ablation, laser ablation or mechanical ablation), the snare 12 can readily be adjusted. According to particularly suitable approach, the cutting operation is directly controlled by appropriately tightening the snare 12 in order to guide the first tubular means 10 from a position close to the wall of the heart chamber 40 towards a position farther away from that wall 40. In other words, the cutting movement may be directed away from the wall of the heart chamber 40 in order to reduce the risk of perforations of the wall.

After completion of the cutting operation, i.e., after sufficiently exposing the capsule 30, particularly, the circumferential capture groove 34 of the same, the snare 12 of the first tubular means 10 is disengaged from the circumferential groove 24 of the second tubular means 20. This action may be facilitated by appropriate rotation of the first tubular means 10 and/or angular movement of the snare 12. Such an angular movement of the snare 12 may be enabled by arranging the snare 12 in a rotatable manner with respect to the first tubular means 10. In particular, the snare 12 may be rotatable with respect to a longitudinal and/or latitudinal axis of the first tubular means 10.

After removal of the snare 12 from the circumferential groove 24 of the second tubular means 20, the snare 12 is engaged to the capsule 30 via the circumferential capture groove 34 of the capsule 30. By pulling and rotating the capsule 30 by appropriate operation of the first tubular means 10 the capsule is disconnected from the wall of the heat chamber 40 and completely separated from fibrosis tissue 50. Subsequently, the capsule 30 can be retrieved from the patient's body by an appropriate pulling movement of the first tubular means 10 that is connected to the capsule 30 via the snare 12 (transvenous ex-traction). In this procedure steps, the tubular means 20 is first unscrewed from the tissues and then moved out from the snare 12. Alternatively, the first tubular means 10 is used for cutting the fibrosis tissue only and the capsule 3 is removed from the patient's body by a different device.

Figure 6:
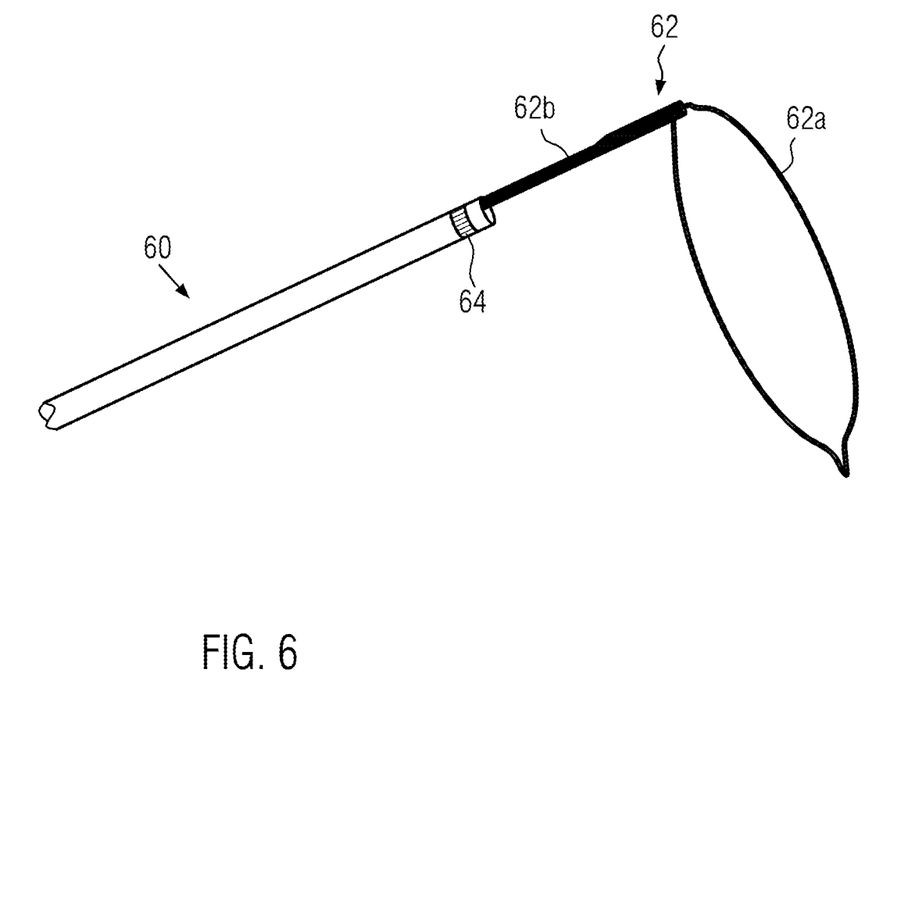
FIG. 6 shows a medical device according to an embodiment that comprises a guiding catheter and a snare.

FIG. 6 illustrates a medical device comprising a guiding catheter 60 and a snare 62. The guiding catheter 60 may be similar to the one employed in the previously described embodiments. As shown, the snare 62 comprises a loop portion 62a and a single linear arm/branch (for example, a mono-fiber portion) 62b extending to the loop portion 62a. When the snare 62 is retracted into the catheter 60, the loop portion 62a gets closed. The guiding catheter 60 may be comprised of a tubular element and a mesh. The loop portion 62a may be made of a highly elastic material. Choice of a highly elastic material for the loop portion 62a of the snare 62 prevents breakage caused by the pumping action of the heart.

Figure 7:
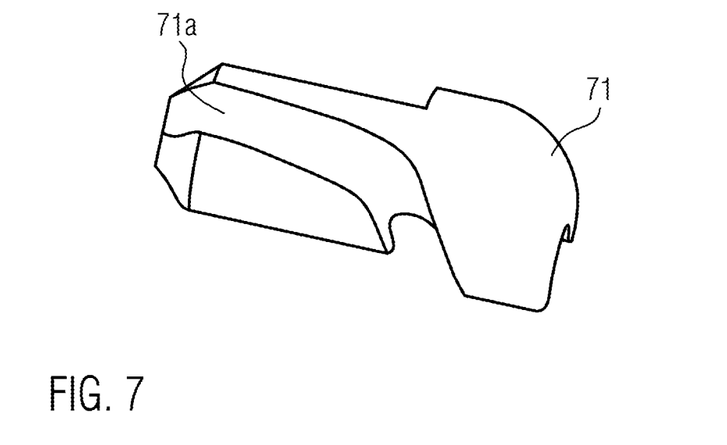
FIG. 7 shows a tip element that can be provided on an end portion of the guiding catheter of FIG. 6.

Additionally, the catheter 60 may be provided with means for controlling (transfer of) a torque between the guiding catheter 60 and the snare 62. The means for controlling the torque may be provided in form of a tip element 71 as it is illustrated in FIG. 7. The tip element 71 may be attached to or may be made of a part of the guiding catheter 60 and allows for maintaining a fixed spatial relationship between the catheter 60 and a portion of the snare 62 that is attached to the catheter 60 by the tip element 71. In particular, the tip element 71 may comprise at least one guiding groove 71a for accommodating a part of the snare 62 as it is illustrated in FIG. 7.

Moreover, a radio-opaque marker 64 is provided at the end portion of the catheter 60 (see FIG. 6). A similar radio-opaque marker may be provided at an end portion of the catheter 10 employed in the previously described embodiments. The radio-opaque marker 64 allows for accurate positioning under X-ray monitoring control.

As illustrated in FIGS. 6 and 7, a medical device is provided comprising a guiding catheter 60 and a snare 62, wherein the snare 62 comprises a loop portion 62a and a mono-fiber portion 62b. Moreover, a tip element 71 can be provided for fixing the snare 62 with respect to the guiding catheter 60 when a torque is applied to the latter by a surgeon. The configurations shown in FIGS. 6 and 7 are particularly suitable in the context of cardio-surgery (confer description above).

All previously discussed embodiments are not intended as limitations, but serve as examples illustrating features and advantages of the disclosure. It is to be understood that some or all of the above described features can also be combined in different ways.

The invention claimed is:

1. An explantation assembly for retrieving an intracorporeal capsule implanted in a tissue of a patient, comprising:
a first tube comprising a sheath, a snare, and a tissue cutter, wherein the sheath is configured to guide both the snare and the tissue cutter for cutting free the intracorporeal capsule, and wherein the snare is coupled to an end of the first tube; and
a second tube, spaced apart laterally from the sheath of the first tube, configured to interact with the snare of the first tube at an end of the second tube to free the intracorporeal capsule and comprising an anchoring member to attach the end of the second tube to the tissue of the patient,
wherein the first tube and the second tube of the explanation assembly are distinct from the intracorporeal capsule.

2. The explantation assembly according to claim 1, wherein the second tube is in direct contact with the snare of the first tube.

3. The explantation assembly according to claim 1, wherein the tissue cutter comprises at least one of a laser, an electrode, or a blade.

4. The explantation assembly according to claim 3, wherein the tissue cutter is a blade, and wherein the blade is retractable into a body of the first tube.

5. The explantation assembly according to claim 1, wherein the snare comprises a loop portion and a linear arm portion extending to the loop portion.

6. The explantation assembly according to claim 1, wherein the second tube comprises a circumferential groove formed in a surface of the second tube and configured to receive the snare of the first tube.

7. The explantation assembly according to claim 1, wherein the anchoring member comprises a helical anchoring member configured to be attached to the tissue of the patient.

8. The explantation assembly according to claim 1, wherein at least one of the first tube or the second tube comprises a central lumen configured for administering a contrast medium or a stylet or a guidewire.

9. The explantation assembly according to claim 1, wherein at least one of the first tube or the second tube comprises a radio-opaque marker and/or is configured to be guided to the tissue of the patient transvenously.

10. The explantation assembly according to claim 1, wherein the snare is rotatable with respect to a longitudinal axis of the first tube and/or the snare is made of a deformable material, comprising a shape memory metal or a material comprising a shape metal alloy.

11. The explantation assembly according to claim 1, wherein the intracorporeal capsule implanted in the tissue of the patient on a wall of a heart chamber of the patient comprises or consists of a cardiac pacemaker.

12. The explantation assembly according to claim 1, wherein the first tube comprises a tip element comprising at least two guiding grooves arranged in parallel to each other for guiding a portion of the snare offset from a longitudinal axis of the first tube.

13. A medical device, comprising:
a first tube comprising a sheath and a snare, the first tube for freeing an intracorporeal capsule, the snare comprising a loop portion and a linear arm portion extending to the loop portion, wherein the snare is coupled to an end of the first tube, and wherein, during operation of the medical device, the loop portion of the snare is supported by an end of a second tube, the second tube attached to a tissue of the patient by an anchoring member; and
a tip element for controlling a torque between the sheath and the snare,
wherein the first tube and the second tube of the medical device are distinct from the intracorporeal capsule, and wherein the second tube is spaced laterally from the sheath of the first tube.

14. The medical device according to claim 13, wherein the tip element is attached to or is a part of the sheath.

* * * * *